United States Patent
Gilbertson et al.

(10) Patent No.: US 9,464,295 B2
(45) Date of Patent: *Oct. 11, 2016

(54) USE OF MULTIPLE TRANSFORMATION ENHANCER SEQUENCES TO IMPROVE PLANT TRANSFORMATION EFFICIENCY

(71) Applicant: Monsanto Technology LLC, St. Louis, MO (US)

(72) Inventors: Larry A. Gilbertson, Chesterfield, MO (US); Xudong Ye, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/295,096

(22) Filed: Jun. 3, 2014

(65) Prior Publication Data

US 2015/0013031 A1    Jan. 8, 2015

Related U.S. Application Data

(62) Division of application No. 13/847,127, filed on Mar. 19, 2013, now Pat. No. 8,759,616, which is a division of application No. 13/035,916, filed on Feb. 25, 2011, now Pat. No. 8,404,931, which is a division of application No. 11/779,739, filed on Jul. 18, 2007, now Pat. No. 7,928,291.

(60) Provisional application No. 60/831,814, filed on Jul. 19, 2006.

(51) Int. Cl.
C12N 15/84       (2006.01)
C12N 15/82       (2006.01)

(52) U.S. Cl.
CPC ....... *C12N 15/8205* (2013.01); *C12N 15/8202* (2013.01)

(58) Field of Classification Search
None
See application file for complete search history.

(56) References Cited

U.S. PATENT DOCUMENTS

| | | |
|---|---|---|
| 5,004,863 A | 4/1991 | Umbeck |
| 5,159,135 A | 10/1992 | Umbeck |
| 5,591,616 A | 1/1997 | Hiei et al. |
| 5,608,142 A | 3/1997 | Barton et al. |
| 5,750,871 A | 5/1998 | Moloney et al. |
| 5,846,797 A | 12/1998 | Strickland |
| 5,981,840 A | 11/1999 | Zhao et al. |
| 6,384,301 B1 | 5/2002 | Martinell et al. |
| 6,624,344 B1 | 9/2003 | Rangan et al. |
| 7,060,876 B2 | 6/2006 | Hiei et al. |
| 7,303,909 B2 | 12/2007 | Heim et al. |
| 7,601,536 B2 | 10/2009 | Rommens et al. |
| 7,682,829 B2 | 3/2010 | Cai et al. |
| 7,749,751 B2 | 7/2010 | Depicker et al. |
| 7,928,291 B2 | 4/2011 | Gilbertson et al. |
| 7,989,678 B2 | 8/2011 | Mankin et al. |
| 2003/0140376 A1 | 7/2003 | Depicker et al. |
| 2004/0244075 A1 | 12/2004 | Cai et al. |
| 2006/0041956 A1 | 2/2006 | Lassner et al. |
| 2006/0070137 A1 | 3/2006 | Rommens et al. |
| 2011/0197311 A1 | 8/2011 | Gilbertson et al. |

FOREIGN PATENT DOCUMENTS

| | | |
|---|---|---|
| CN | 2 148 499 | 7/2006 |
| EP | 672752 | 9/1995 |
| WO | WO 95/05471 | 2/1995 |
| WO | WO 95/06722 | 3/1995 |
| WO | WO 00/18939 | 4/2000 |
| WO | WO 01/44482 | 6/2001 |
| WO | WO 2005/121346 | 12/2005 |
| WO | WO 2006/024509 | 3/2006 |

OTHER PUBLICATIONS

Albright et al., "Processing of the T-DNA of agrobacterium tumefaciens generates border nicks and linear, single-stranded T-DNA," *J. Bacteriol.*, 169(3):1046-1055, 1987.
Barker et al., "Nucleotide sequence of the T-DNA region from the agrobacterium tumefaciens octopine Ti plasmid pTi15955,", *Plant Mol. Biol.*, 2:335-350, 1983.
Bouchez et al., *Plasmid* 25:27-39, 1991.
Breitler at al., *Transgenic Research* 13:271-287, 2004.
Broothaerts at al., "Gene transfer to plants by diverse species of bacteria," *Nature*, 433:629-633, 2005.
Canaday et al., "Organization and functional analysis of the three T-DNAs from the vitopine Ti plasmid pTiS4," *Mol. Gen. Genet.*, 235:292-303, 1992.
Close et al., "Dual control of agrobacterium tumefaciens Ti plasmid virulence genes," *J. Bacteriol.*, 169(11):5113-5118, 1987.
Culianez-Macia et al., "Right border sequences enable the left border of an agrobacterium tumefaciens nopaline Ti-plasmid to produce single-stranded DNA," *Plant Mol. Bio.*, 11:389-399, 1988.
GenBank Accession No. AF242881, Dec. 22, 2006.
GenBank Accession No. AJ271050, Jan. 14, 2000.
GenBank Accession No. M63056, Apr. 26, 1993.
Gould at al., "Transformation of *Zea mays* L. using agrobacterium tumefaciens and the shoot apex," *Plant Physiol.*, 95:426-434, 1991.
Griffiths, "A Nopaline-type *Overdrive* Element, and its influence upon *Agrobacterium*-mediated Transformation Frequency and T-DNA Copy Number in *Nicotiana tabacum*," Ph.D. Thesis, Massey University, Palmerston North, New Zealand/Aotearoa, 1996.

(Continued)

*Primary Examiner* — David T Fox
(74) *Attorney, Agent, or Firm* — Dentons US LLP

(57) ABSTRACT

The present invention relates to methods and compositions for improving the efficiency of *Agrobacterium*- and *Rhizobium*-mediated plant cell transformation by use of additional transformation enhancer sequences, such as overdrive or TSS sequences, operably linked to a T-DNA border sequence on a recombinant construct that comprises T-DNA.

45 Claims, 4 Drawing Sheets

(56) References Cited

OTHER PUBLICATIONS

Hanson et al., "A T-DNA transfer stimulator sequence in the vicinity of the right border of pRi8196," *Plant Mol. Biol.*, 20(1):113-122, 1992.
Hepburn et al., "The effect of right terminal repeat deletion on the oncogenicity of the T-region of pTiT37," *Plant Mol. Biol.*, 5(1):3-11, 1985.
Jen et al., "The right border region of pTiT37 T-DNA is intrinsically more active than the left border region in promoting T-DNA transformation," *Proc. Natl. Acad. Sci USA*, 83(11):3895-3899, 1986.
Mankin et al., Sequence 1 of US 20070292953, 2007.
Park et al., "Shorter T-DNA or additional virulence genes improve agrobactrium-mediated transformation," *Theor. Appl. Genet.*, 101:1015-1020, 2000.
Peralta et al., "Overdrive, a T-DNA transmission enhancer on the A. tumefaciens tumour-inducing plasmid," *EMBO J.*, 5:1137-1142, 1986.
Rommens et al., "All-native DNA transformation: a new approach to plant genetic engineering," *Trends in Plant Science*, 9(9):457-464, 2004.
Rommens et al., "Crop improvement through modification of the plant's own genome," *Plant Physiol.*, 135:421-431, 2004.
Rommens et al., "Plant-Derived Transfer DNAs," *Plant Physiol.*, 139:1338-1349, 2005.
Shaw et al., "The right hand copy of the nopaline Ti-plasmid 25 by repeat is required for tumour formation," *Nucleic Acids Res.* 12(15):6031-6041, 1984.
Shurvinton et al., "Stimulation of agrobacterium tumefaciens T-DNA transfer by overdrive depends on a flanking sequence but not on helical position with respect to the border repeat," *J. Bacteriol.*, 173(17):5558-5563, 1991.
Slightom et al., "Isolation and identification of TL-DNA/plant junctions in convolvulus arvensis transformed by agrobacterium rhizogenes strain A4," *EMBO J.*, 4(12):3069-3077, 1985.
Slightom et al., "Nucleotide sequence analysis of the TL-DNA of agrobacterium rhizogenes agropine type plasmid," *J. Biol. Chem.*, 261:108-121, 1986.
Toro et al., "The agrobacterium tumefaciens virC1 gene product binds to overdrive, a T-DNA transfer enhancer," *J. Bacteriol.*, 171(12):6845-6849, 1989.
Toro et al., "Role of the overdrive sequence in T-DNA border cleavage in agrobacterium," *Proc. Natl. Acad. Sci. USA*, 85:8558-8562, 1988.
Van Haaren et al., "Function of heterologous and pseudo border repeats in T-region transfer via the octopine virulence system of agrobacterium tumefaciens," *Plant Mol. Biol.*, 11:773-781, 1988.
Van Haaren et al., "Functional analysis of the agrobacterium tumefaciens octopine Ti plasmid left and right T-region border fragments," *Plant Mol. Biol.*, 8:95-104, 1987.
Van Haaren et al., "Overdrive is a T-region transfer enhancer which stimulates T-strand production in agrobacterium tumefaciens," *Nucleic Acids Res.*, 15(21):8983-8997, 1987.
Veluthambi et al., "Virulence genes, borders, and overdrive generate single-stranded T-DNA molecules from the A6 Ti plasmid of agrobacterium tumefaciens," *J. Bacteriol.*, 170(4):1523-1532, 1988.
Wang et al., "Sequence context of the T-DNA border repeat element determines its relative activity during T-DNA transfer to plant cells," *Mol. Gen. Genet.*, 210:338-346, 1987.
Wang et al., "Site-specific nick in T-DNA border sequence as a result of agrobacterium vir gene expression," *Science*, 235:587-591, 1987.
Zhang et al., "The use of glufosinate as a selective agent in agrobacterium-mediated transformation of soybean," *Plant Cell Tiss.Org. Cult.*, 56:37-46, 1999.

(A)
Nopaline RB+1x overdrive
AGGATTTTTCGGCGCTGCGCTACGTCCGCGACCGCGTTGAGGGATCAAGCCA
CAGCAGCCCACTCGACCTTCTAGCCGACCCAGACGAGCCAAGGGATCTTTTTGGAAT
GCTGCTCCGTCGTCAGGCTTTCCGACGTTTGGGTGGTTGAACAGAAGTCATTATCGC
ACGGAATGCCAAGCACTCCCGAGGGGAACCCTGTGGTTGGCATGCACATACAAATG
GACGAACGGATAAACCTTTTCACGCCCTTTTAAATATCCGATTATTCTAATAAACGC
TCTTTcaaacaaacatacacagcgacttattcacaTCTCTTAG<u>GTTTACCCGCCAATATATCCTGTCA</u>
<u>AACACTGATAGTTTAAACTGAAGGCGGGAAACGACAATCT</u>

(B)
Nopaline RB+4x overdrive
AGGATTTTTCGGCGCTGCGCTACGTCCGCgACCGCGTTGAGGGATCAAGCCAC
AGCAGCCCACTCGACCtTCTAGCCGACCCAGACGAGCCAAGGGATCTTTTTGGAATG
CTGCTCCGTCGTCAGGCTTTCCGACGTTTGGGTGGTTGAACAGAAGTCATTATCGcAC
GGAATGCCAAGCACTCCCGAGGGGAACCCTGTGGTTGGCATGCACATACAAATGGA
CGAACGGATAAACCTTTTCACGCCCTTTTAAATATCCGaTTATTCTAATAAACGCTCT
TTGAATTCGCCCTTcaaacaaacatacacagcgacttattcacacaaacaaacatacacagcgacttattcacacaaac
aaacatacacagcgacttattcacacaaacaaacatacacagcgacttattcacaAAGGGCGAATTCTCTTAG<u>GT</u>
<u>TTACCCGCCAATATATCCTGTCA</u>AACACTGATAGTTTAAACTGAAGGCGGGAAACGA
CAATCT

(C)
Nopaline RB+18x TSS
AGGATTTTTCGGCGGCGCTACGTCCGCgACCGCGTTGAGGGATCAAGCCACA
GCAGCCCACTCGACCtTCTAGCCGACCCAGACGAGCCAAGGGATCTTTTTGGAATGC
TGCTCCGTCGTCAGGCTTTCCGACGTTTGGGTGGTTGAACAGAAGTCATTATCGcACG
GAATGCCAAGCACTCCCGAGGGGAACCCTGTGGTTGGCATGCACATACAAATGGAC
GAACGGATAAACCTTTTCACGCCCTTTTAAATATCCGaTTATTCTAATAAACGCTCTT
TGAATTCGCCCTTctgacgaactgacgaactgacgaactgacgaactgacgaactgacgaactgacgaactgacgaac
tgacgaactgacgaactgacgaactgacgaactgacgaactgacgaactgacgaactgacgaactgacgaaGGG
CGAATTCTCTTAG<u>GTTTACCCGCCAATATATCCTGTCA</u>AACACTGATAGTTTAAACTG
AAGGCGGGAAACGACAATCT

FIG. 4

USE OF MULTIPLE TRANSFORMATION ENHANCER SEQUENCES TO IMPROVE PLANT TRANSFORMATION EFFICIENCY

This application is a divisional of U.S. application Ser. No. 13/847,127, filed Mar. 19, 2013, now U.S. Pat. No. 8,759,616, which application is a divisional of U.S. application Ser. No. 13/035,916, filed Feb. 25, 2011, now U.S. Pat. No. 8,404,931, which application is a divisional of U.S. application Ser. No. 11/779,739, filed Jul. 18, 2007, now U.S. Pat. No. 7,928,291, which application claims the priority of U.S. Provisional Patent Application Ser. No. 60/831,814, filed Jul. 19, 2006, the disclosures of all of which are incorporated herein by reference in their entirety.

BACKGROUND OF THE INVENTION

1. Field of the Invention

The invention relates generally to plant biotechnology. More specifically, the invention relates to methods and compositions for improving the efficiency of bacterially-mediated plant transformation.

2. Description of Related Art

During natural *Agrobacterium*-mediated transformation of plant cells, a piece of DNA from the Ti plasmid of *A. tumefaciens* or Ri plasmid of *A. rhizogenes* is transferred into the plant cell (e.g. Gelvin, 2003). This transferred DNA (T-DNA) fragment is flanked by imperfect 24 bp direct repeats that are recognized by *Agrobacterium* endonuclease VirD2 to produce a single stranded T-strand by nicking at a specific site in one strand of each repeat. The repeat that initiates formation of single stranded T-strand has been termed the "right border" (RB), while the repeat terminating formation of single-stranded T-DNA has been termed the "left border" (LB). The VirD2 protein is attached to the 5' end of the strand after nicking, and guides the T-strand into plant cells where the T-strand is integrated into the plant genome with the help of other *Agrobacterium* and plant-encoded proteins. Sequences downstream (in a 5' to 3' direction) of the T-DNA region, including vector backbone sequence, may be transferred as well (e.g. Kononov et al., 1997). This likely occurs by inefficient nicking of at least one of the borders in *Agrobacterium* prior to transfer to a plant cell.

Comparison of the RB and LB sequences from a variety of *Agrobacterium* strains indicated that both RB and LB share a consensus motif (Canaday et al., 1992), which indicates that other elements may be involved in modulating the efficiency of RB processing. Cis-acting sequences next to the RB are present in many *Agrobacterium* strains, including *A. tumefaciens* and *A. rhizogenes*. These sequences are necessary for wild type virulence (Veluthambi et al., 1988; Shurvington and Ream, 1991; Toro et al., 1989; Toro et al., 1988; Hansen et al., 1992). The sequence in *A. tumefaciens* was called an "overdrive" or "T-DNA transmission enhancer" by Peralta et al., (1986). In *A. rhizogenes* the sequence has been termed the "T-DNA transfer stimulator sequence" (TSS) by Hansen et al (1992). The overdrive ("OD") sequence was initially defined as a particular 24 bp motif present immediately in front of the RB repeat of octopine Ti TL-DNA (Peralta et al., 1986). A similar sequence is present in front of the RB repeat of octopine Ti TR-DNA and also in front of nopaline Ti RB and agropine Ri TL right border (Peralta et al., 1986, Shaw et al., 1984, Barker et al., 1983, Slighton et al., 1985). Further comparison of different *A. tumefaciens* strains revealed a 8 bp overdrive core sequence present in front of all right border sequences including nopaline strain pTiT37, octopine strain pTiA6 and *A. rhizogenes* pRiA4 (Peralta et al., 1986).

The presence of octopine overdrive sequence enhanced single strand T-DNA formation in *Agrobacterium* cells and improved T-DNA transfer into plant cells, and was necessary for wild type virulence (Peralta et al., 1986, Shurvinton and Ream 1991). The LB repeat from nopaline-producing Ti plasmid pTiT37 is capable of producing single-stranded T-DNA with high efficiency when the pTiT37 RB proximal cis-acting sequence was placed in front of it, indicating that an overdrive-like sequence indeed is also present on a nopaline Ti plasmid (Culianez-Macia and Hepburn 1988, Peralta et al., 1986), just as it is in the other identified (octopine-producing) Ti plasmids. Integration of a heterologous octopine overdrive sequence in front of nopaline pTiT37 RB resulted in much greater virulence than the parental strain which contained only a synthetic pTiT37 RB repeat (Peralta et al., 1986).

The VirC1 protein binds to overdrive and is thought to improve VirD2 nicking (Toro et al., 1988, 1989), while mutation of virC results in attenuated virulence in plants (Close et al., 1987) and reduced production of processed single stranded T-DNA sequence. Both *A. tumefaciens* octopine and nopaline Ti plasmids contain virC and can complement the virC mutation in trans to restore the attenuated virulence to wild type level (Close et al., 1987).

The TSS found in *A. rhizogenes* strains 8196, A4 and 2659 plays a similar role as the overdrive sequence in *A. tumefaciens*. Each *A. rhizogenes* strain has a different but related sequence (Hansen et al., 1992). The 8 bp TSS core sequence repeats 5 times in pRiA4, 6 times in pRi8196 and 17 times (rather than 16× as Hansen et al., 1992) in pRi2659 (Genbank accession AJ271050). pRiA4 has a conserved 8 bp overdrive core sequence in addition to the repeats. Shorter core sequence repeats in pRiA4 and pRi8196 were not sufficient for wild type virulence (Hansen et al., 1992).

Depicker et al. (U.S. Patent Publication 2003/0140376, and corresponding international publication WO01/44482) describe recombinant constructs with modified T-DNA borders in order to lessen or prevent transference of vector backbone sequences. Conner et al., (WO 05/121346) describe creation and use of sequences from T-DNA border-like regions that comprise sequences derived from plants. Heim et al. (U.S. Publ. 2003/0188345) describe vectors for *Agrobacterium*-mediated transformation of plants with modified border regions. Lassner et al., (U.S. Publ. 2006/0041956) describe modifications to T-DNA border regions to enable identification of transgenic events that do not comprise non T-DNA sequences.

While the foregoing studies have increased understanding in the art, what remains needed is a method to improve the efficiency of *Agrobacterium*-mediated plant transformation. Although the presence of overdrive or TSS sequences increases virulence of wild type *Agrobacterium* and improves T-DNA transfer into plant cells compared to plasmids lacking the sequences, it has remained unclear how to further improve transformation efficiency including through the use of overdrive or TSS sequences.

SUMMARY OF THE INVENTION

In one aspect, the invention provides a method of increasing the efficiency of bacterially-mediated plant transformation, comprising the steps of: a) introducing at least one additional transformation enhancer sequence into a plant transformation vector comprising at least one T-DNA border region; and b) transforming a plant cell with the vector by bacterially-mediated transformation, wherein the bacterium is competent for the transformation of the plant cell. The method may optionally comprise regenerating a transgenic plant from the plant cell. In one embodiment, the additional transformation enhancer sequence comprises a consensus core sequence of TGTWTGTK (SEQ ID NO:20). In other embodiments, the additional transformation enhancer sequence is selected from the group consisting of: SEQ ID NO:6, SEQ ID NO:7, SEQ ID NO:8, SEQ ID NO:9, SEQ ID NO:13, and a sequence complementary to any of SEQ ID NO:6, SEQ ID NO:7, SEQ ID NO:8, SEQ ID NO:9, or SEQ ID NO:13. In particular embodiments, the invention provides a recombinant DNA construct comprising SEQ ID NO:14, SEQ ID NO:15, or SEQ ID NO:16.

The transformation enhancer sequence used with the invention may be located proximal to a T-DNA border region or sequence, such as a right border (RB) sequence, i.e. between flanking sequence such as vector sequence and the border sequence. The transformation enhancer sequence may be from a Ti plasmid of *A. tumefaciens*, such as a nopaline or octopine plasmid, or may be from an Ri plasmid of *A. rhizogenes*. In certain embodiments, the bacterially-mediated transformation may utilize a technique selected from *Agrobacterium*-mediated transformation, *Rhizobium*-mediated transformation, and *Sinorhizobium*-, *Mesorhizobium*- or *Bradyrhizobium*-mediated transformation. In certain embodiments, the transformation enhancer sequence may comprise SEQ ID NO:10, SEQ ID NO:11, SEQ ID NO:17, or SEQ ID NO:18. In further embodiments, the T-DNA border region may comprise from 1 to about 18 copies of the transformation enhancer sequence, including from about 2 or about 4 to about 18 copies of the transformation enhancer sequence.

A plant cell in accordance with the invention may be any plant cell. In certain embodiments, the plant cell is from a plant selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato and watermelon. In particular embodiments, the plant cell is a corn cell or a soybean cell.

In another aspect, the invention provides a recombinant DNA construct comprising a T-DNA border sequence of a Ti or Ri plasmid, operably linked to a transformation enhancer sequence that comprises two or more copies of a sequence selected from the group consisting of: SEQ ID NO:6, SEQ ID NO:7, SEQ ID NO:8, SEQ ID NO:9, SEQ ID NO:13, a sequence complementary to any of SEQ ID NO:6, SEQ ID NO:7, SEQ ID NO:8, SEQ ID NO:9, or SEQ ID NO:13, and combinations thereof. In particular embodiments, the invention provides a recombinant DNA construct comprising SEQ ID NO:14, SEQ ID NO:15, or SEQ ID NO:16.

In such a construct, the enhancer sequence may comprise at least about four copies of the sequence. The border sequence may be a right border (RB) or left border (LB) sequence. In certain embodiments, the construct may comprise SEQ ID NO:10 and/or SEQ ID NO:11. The RB sequence may be from a nopaline Ti plasmid, or an agropine, mannopine, succimanopine, cucumopine, or octopine Ti or Ri plasmid and may comprise SEQ ID NO:12.

In another aspect, the invention provides a cell transformed with a construct provided herein. The cell may be a plant or bacterial cell, including an *Agrobacterium* cell and *Rhizobium* cell. In one embodiment, the plant cell is from a plant selected from the group consisting of soybean, corn, cotton, canola, rice, wheat, alfalfa, common bean, peanut, tobacco and sunflower. The invention also provides transgenic plants transformed a construct of the invention. In particular embodiments, the transgenic plant may be selected from the group consisting of soybean, corn, cotton, canola, rice, wheat, alfalfa, common bean, peanut, tobacco and sunflower.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 4: Engineered RB sequences; overdrive sequence is in bold and the 24 bp RB core sequence underlined. (A) sequence of the Nopaline RB+1× overdrive (SEQ ID NO:14); (B) Nopaline RB+4× overdrive (SEQ ID NO:15); (C) Nopaline RB+18×TSS (SEQ ID NO:16).

DESCRIPTION OF SEQUENCE LISTING

Figure 1:
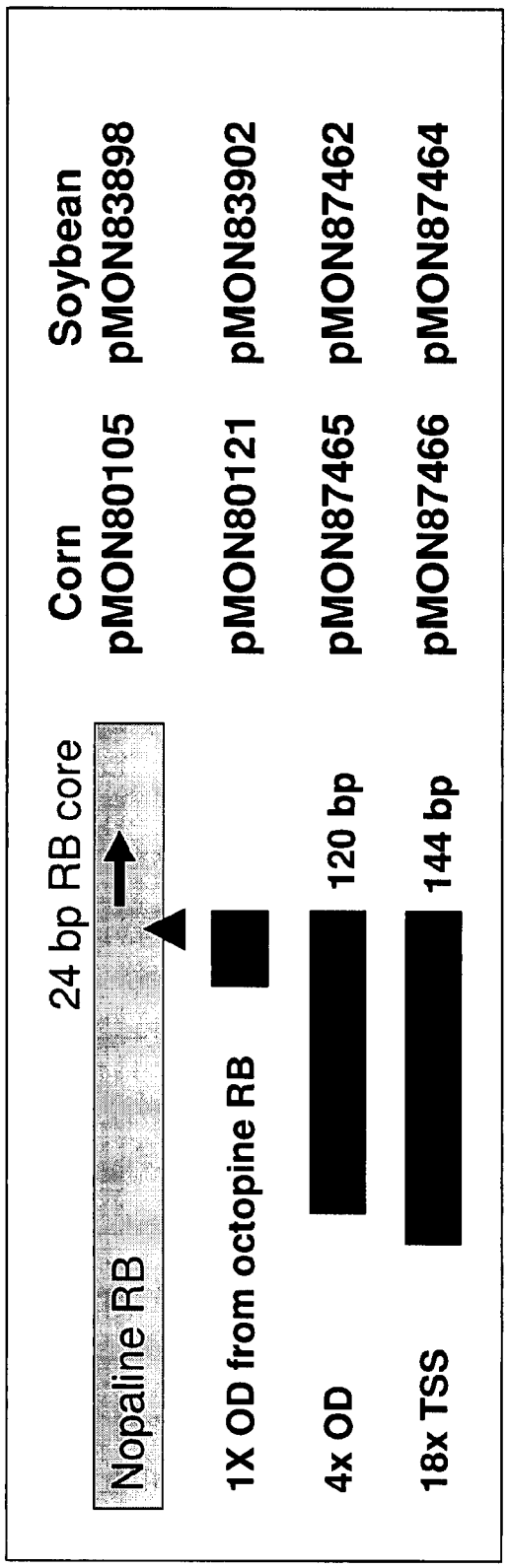
FIG. 1: Outline of various transformation enhancer sequences used for improving transformation efficiency.
Figure 2:
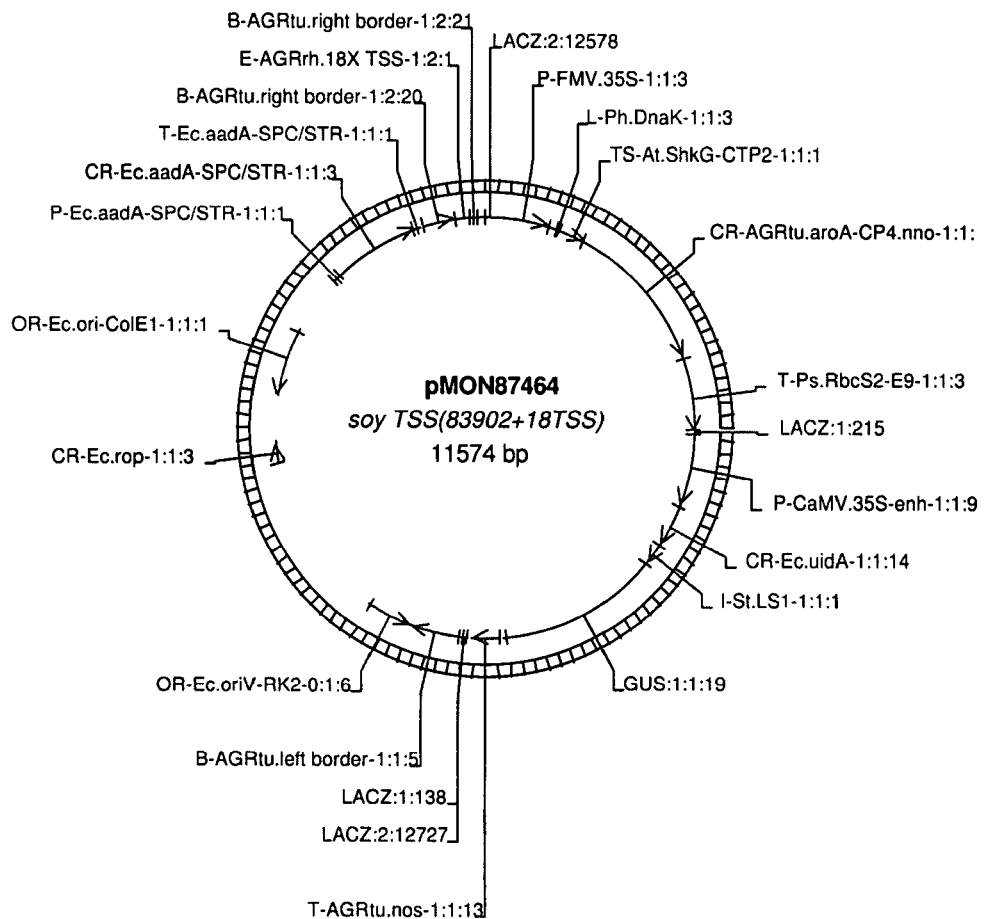
FIG. 2: Schematic map of pMON87464.
Figure 3:
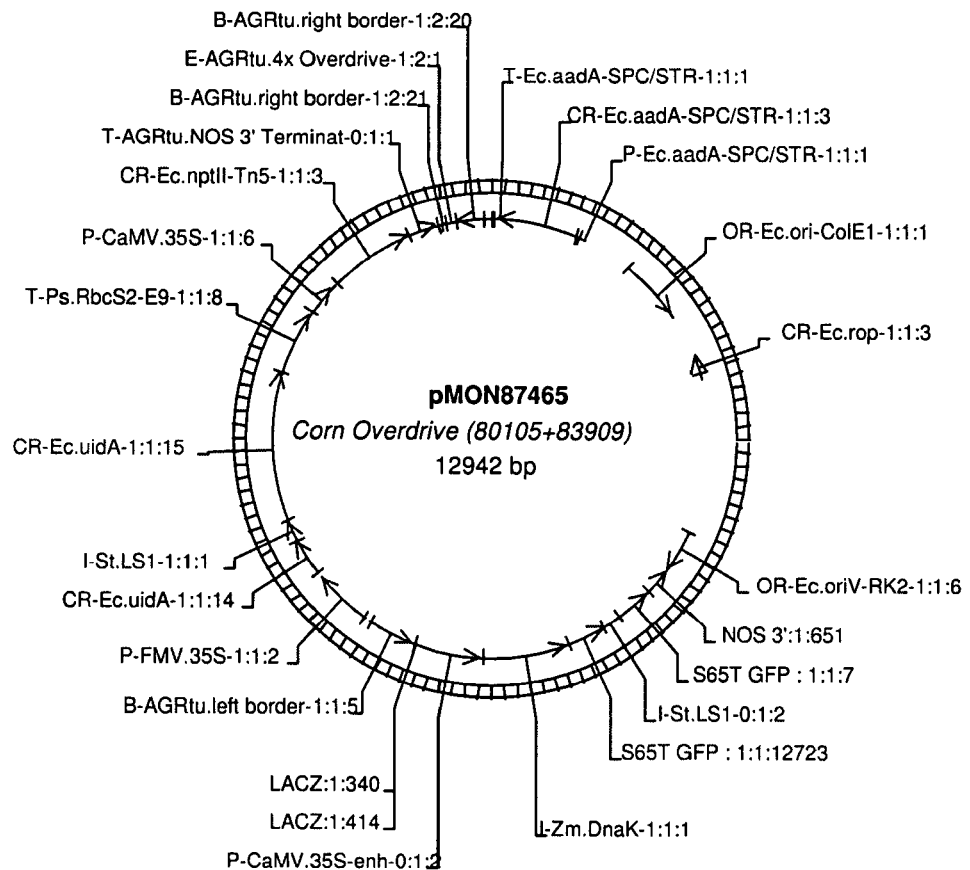
FIG. 3: Schematic map of pMON87465.

SEQ ID NO:1 Forward primer Xd463 for 2×OD sequence preparation.
SEQ ID NO:2 Reverse primer Xd464 for 2×OD sequence preparation.
SEQ ID NO:3 Forward primer Xd465 for 6×TSS sequence preparation.
SEQ ID NO:4 Reverse primer Xd466 for 6×TSS sequence preparation.
SEQ ID NO:5 24 bp core OD of pTiA6.
SEQ ID NO:6 8 bp 1×TSS sequence.
SEQ ID NO:7 30 bp 1×OD of pTiA6; reverse complement of SEQ ID NO:17.
SEQ ID NO:8 1×OD sequence from pTiAB3.
SEQ ID NO:9 1×OD from pTi15955.
SEQ ID NO:10 4× stacked OD.
SEQ ID NO:11 18× stacked TSS.
SEQ ID NO:12 Border region with 1×OD sequence.
SEQ ID NO:13 Partial OD sequence.
SEQ ID NO:14 Nopaline RB region with 1×OD.
SEQ ID NO:15 Nopaline RB region with 4×OD.
SEQ ID NO:16 Nopaline RB region with 18×TSS.
SEQ ID NO:17 1×OD; reverse complement of SEQ ID NO:7.
SEQ ID NO:18 4× stacked OD; reverse complement of SEQ ID NO:10.
SEQ ID NO:19 Consensus OD sequence (Toro et al., 1988).
SEQ ID NO:20 Consensus 8 bp core OD sequence.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The invention provides methods and compositions for improving the efficiency of *Agrobacterium*-mediated transformation of plant cells. Sequencing of the 20 kb T-DNA region of *A. rhizogenes* K599, a soybean super virulent strain, led to the recognition that the pRi plasmid in *A. rhizogenes* K599 is identical to the *A. rhizogenes* NCPBB 2659 strain. The super-virulence of the K599 strain may thus be related to the number of TSS sequences present near the RB. Therefore, stacking of multiple overdrive and TSS repeats was tested in binary vectors with a nopaline RB (e.g. from pTiT37) to improve transformation efficiency. The octopine Ti plasmid's 30 bp overdrive (Shurvinton and Ream 1991) from pTiA6, present in 4 copies, and the *A. rhizogenes* NCPBB2659 TSS 8 bp core sequence, present in 18 copies, was used to enhance T-DNA transmission efficiency.

Transformation studies comparing the use of constructs containing varying numbers of overdrive or TSS sequences demonstrated that the presence of additional "stacked" copies of these sequences improved transformation efficiency by improving transformation frequency as well as the quality of the resulting transgenic events. For example, the proportion of events with single copy insertions, and also lacking vector backbone sequences (e.g. oriV), was increased. Increased transformation frequency and quality events improve the overall efficiency of the transformation process by reducing the amount of resources required to select event for further commercial development.

The invention therefore provides improved methods for obtaining fertile transgenic plants and for the transformation of plant cells or tissues and regeneration of the transformed cells or tissues into fertile transgenic plants. To initiate a transformation process in accordance with the invention, the genetic components desired to be inserted into the plant cells or tissues will first be selected. Genetic components may include any nucleic acid that is to be introduced into a plant cell or tissue using the method according to the invention. Genetic components can include non-plant DNA, plant DNA, or synthetic DNA.

In certain embodiments of the invention, genetic components are incorporated into a DNA composition such as a recombinant, double-stranded plasmid or vector molecule comprising genetic components such as: (a) a promoter that functions in plant cells to cause the production of an RNA sequence, (b) a structural DNA sequence that causes the production of an RNA sequence that encodes a desired protein or polypeptide, and (c) a 3' non-translated DNA sequence that functions in plant cells to cause the polyadenylation of the 3' end of the RNA sequence. The vector may also contain genetic components that facilitate transformation and regulate expression of the desired gene(s).

The genetic components are typically oriented so as to express an mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase and subsequent processing of the mRNA primary transcript inside the nucleus. This processing involves a 3' non-translated region that includes polyadenylation of the 3' ends of the mRNA.

General methods for preparing plasmids or vectors that contain desired genetic components and can be used to transform plants and methods of making those vectors are known in the art. Vectors typically consist of a number of genetic components, including, but not limited to, regulatory elements such as promoters, leaders, introns, and terminator sequences. Regulatory elements are also referred to as cis- or trans-regulatory elements, depending on the proximity of the element to the sequences or gene(s) they control. The promoter region contains a sequence of bases that signals RNA polymerase to associate with the DNA and to initiate the transcription into mRNA using one of the DNA strands as a template to make a corresponding complementary strand of RNA.

The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, EHA101, or EHA105 carrying a plasmid having a transfer function for the expression unit. Other bacterial strains known to those skilled in the art of plant transformation can function in the present invention, including *A. rhizogenes*, *Sinorhizobium* sp., *Mesorhizobium* sp., *Bradyrhizobium* sp., and *Rhizobium* sp. strains.

A number of promoters that are active in plant cells have been described in the literature. Such promoters include, but are not limited to, the nopaline synthase (NOS) and octopine synthase (OCS) promoters, which are carried on tumor-inducing plasmids of *A. tumefaciens*; the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ssRUBISCO, a very abundant plant polypeptide). All of these promoters have been used to create various types of DNA constructs that have been expressed in plants. Promoter hybrids can also be constructed to enhance transcriptional activity or to combine desired transcriptional activity, inducibility, and tissue or developmental specificity.

Thus, promoters that function in plants may be inducible, viral, synthetic, constitutive as described, temporally regulated, spatially regulated, and/or spatio-temporally regulated. Other promoters that are tissue-enhanced, tissue-specific, or developmentally regulated are also known in the art and envisioned to have utility in the practice of this invention. Useful promoters may be obtained from a variety of sources such as plants and plant DNA viruses. It is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA and are usually known as translational enhancers. Other genetic components that serve to enhance expression or affect transcription or translation of a gene are also envisioned as genetic components. The 3' non-translated region of the chimeric constructs preferably contains a transcriptional terminator, or an element having equivalent function, and a polyadenylation signal, which functions in plants to polyadenylate the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (nos) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea.

Typically, DNA sequences located a few hundred base pairs downstream of the polyadenylation site serve to terminate transcription. These DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In many transformation systems, it is preferable that the transformation vector contains a selectable, screenable, or scoreable marker gene. These genetic components are also referred to herein as functional genetic components, as they produce a product that serves a function in the identification of a transformed plant, or a product of desired utility.

The DNA that serves as a selection device may function in a regenerable plant tissue to produce a compound that confers upon the plant tissue resistance to an otherwise toxic compound. Genes of interest for use as a selectable, screenable, or scoreable marker would include, but are not limited to, β-glucuronidase (gus), green fluorescent protein (gfp), luciferase (lux), antibiotics like kanamycin (Dekeyser et al., 1989), genes allowing tolerance to herbicides like glyphosate (Della-Cioppa et al., 1987), such as CP4 EPSPS (U.S. Pat. No. 5,627,061; U.S. Pat. No. 5,633,435; U.S. Pat. No. 6,040,497; U.S. Pat. No. 5,094,945; WO04/074443; WO04/009761); glufosinate (U.S. Pat. No. 5,646,024, U.S. Pat. No. 5,561,236, U.S. Pat. No. 5,276,268; U.S. Pat. No. 5,637,489; U.S. Pat. No. 5,273,894); 2,4-D (WO05/107437) and dicamba, such as DMO (U.S. Pat. No. 7,022,896). Other selection methods can also be implemented, including, but not limited to, tolerance to phosphinothricin, bialaphos, and positive selection mechanisms (Joersbo et al., 1998) and would still fall within the scope of the present invention. Examples of various selectable/screenable/scoreable markers and genes encoding them are disclosed in Miki and McHugh (2004).

The present invention can be used with any suitable plant transformation plasmid or vector containing a selectable or screenable marker and associated regulatory elements as described, along with one or more nucleic acids (a structural gene of interest) expressed in a manner sufficient to confer a particular desirable trait. Examples of suitable structural genes of interest envisioned by the present invention include, but are not limited to, genes for insect or pest tolerance, genes for herbicide tolerance, genes for quality improvements such as yield, nutritional enhancements, environmental or stress tolerances, or genes for any desirable changes in plant physiology, growth, development, morphology, or plant product(s).

Alternatively, the DNA coding sequences can affect these phenotypes by encoding a non-translatable RNA molecule that causes the targeted inhibition of expression of an endogenous gene, for example via double-stranded RNA mediated mechanisms, including antisense- and cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillitoe, 1997). More particularly, for a description of antisense regulation of gene expression in plant cells see U.S. Pat. No. 5,107,065, and for a description of gene suppression in plants by transcription of a dsRNA see U.S. Pat. No. 6,506,559, U.S. Patent Application Publication No. 2002/0168707 A1, and U.S. patent application Ser. No. 09/423,143 (see WO 98/53083), Ser. No. 09/127,735 (see WO 99/53050) and Ser. No. 09/084,942 (see WO 99/61631), all of which are incorporated in their entirety herein by reference.

Use of sequences that result in silencing of other endogenous genes (e.g. RNAi technologies including miRNA) to result in a phenotype is also envisioned. For instance RNAi may be used to silence one or more genes resulting in a scoreable phenotype. One embodiment is to assemble a DNA cassette that will transcribe an inverted repeat of sequences, to produce a double-stranded RNA (dsRNA), typically at least about 19-21 bp in length and corresponding to a portion of one or more genes targeted for silencing. Thus, any gene that produces a protein or mRNA that expresses a phenotype or morphology change of interest is useful for the practice of the present invention.

Exemplary nucleic acids that may be introduced by the methods encompassed by the present invention include, for example, heterologous DNA sequences—that is, sequences or genes from another species, or even genes or sequences that originate with or are present in the same species but are incorporated into recipient cells by genetic engineering methods rather than classical reproduction or breeding techniques. The term heterologous, however, is also intended to refer to genes that are not normally present in the cell being transformed or to genes that are not present in the form, structure, etc., as found in the transforming DNA segment or to genes that are normally present but a different expression is desirable. Thus, the term "heterologous" gene or DNA is intended to refer to any gene or DNA segment that is introduced into a recipient cell, regardless of whether a similar gene may already be present in such a cell. The type of DNA included in the heterologous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene or sequence.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

After the construction of the plant transformation vector or construct, the nucleic acid molecule, prepared as a DNA composition in vitro, is generally introduced into a suitable host such as *Escherichia coli* and mated into another suitable host such as *Agrobacterium* or *Rhizobium*, or directly transformed into competent *Agrobacterium* or *Rhizobium*. These techniques are well-known to those of skill in the art and have been described for a number of plant systems including soybean, cotton, and wheat (see, for example, U.S. Pat. Nos.

5,569,834 and 5,159,135 and WO 97/48814). Those of skill in the art would recognize the utility of *Agrobacterium*-mediated transformation methods. Strains may include, but are not limited to, disarmed derivatives of *A. tumefaciens* strain C58, a nopaline strain that is used to mediate the transfer of DNA into a plant cell; octopine strains, such as LBA4404; or agropine strains, e.g., EHA101, EHA105, or *R. leguminosarum* USDA2370 with a Ti or Ri plasmid. The use of these strains for plant transformation has been reported, and the methods are familiar to those of skill in the art.

Plant tissue to be transformed is typically inoculated and co-cultured with *Agrobacterium* or *Rhizobium* containing a recombinant construct comprising at least one heterologous overdrive or TSS sequence, a sequence of interest to be transferred, and at least one RB sequence that serves to define the DNA to be transferred, and is selected under appropriate conditions. In certain embodiments, at least one LB sequence is also present on the recombinant construct. In certain other embodiments, a border sequence can be a "plant derived border-like sequence(s)." Methods of identifying and using such sequences are described in Rommens et al., 2005; Rommens 2004a; Rommens et al., 2004b The present invention can be used with any transformable cell or tissue. Those of skill in the art recognize that transformable plant tissue generally refers to tissue that can have exogenous DNA inserted in its genome and under appropriate culture conditions can form into a differentiated plant. Such tissue can include, but is not limited to, cell suspensions, callus tissue, hypocotyl tissue, cotyledons, embryos, meristematic tissue, roots, and leaves. For example, transformable tissues can include calli or embryoids from anthers, microspores, inflorescences, and leaf tissues. Other tissues are also envisioned to have utility in the practice of the present invention, and the desirability of a particular explant for a particular plant species is either known in the art or may be determined by routine screening and testing experiments whereby various explants are used in the transformation process and those that are more successful in producing transgenic plants are identified.

Methods for transforming dicots by use of *Agrobacterium* or *Rhizobium* and obtaining transgenic plants have been published for a number of crops including cotton, soybean, *Brassica*, and peanut. Successful transformation of monocotyledonous plants by *Agrobacterium*- or *Rhizobium*-based methods has also been reported. Transformation and plant regeneration have been achieved and reported at least in asparagus, barley, maize, oat, rice, sugarcane, tall fescue, and wheat. Techniques that may be particularly useful in the context of cotton transformation are disclosed in U.S. Pat. Nos. 5,846,797, 5,159,135, 5,004,863, and 6,624,344. Techniques for transforming *Brassica* plants in particular are disclosed, for example, in U.S. Pat. No. 5,750,871. Techniques for transforming soybean are disclosed in for example in Zhang et al., (1999) and U.S. Pat. No. 6,384,301; and techniques for transforming corn are disclosed in for example in U.S. Pat. No. 5,981,840, U.S. Pat. No. 7,060,876, U.S. Pat. No. 5,591,616, WO95/06722, and U.S. Patent Pub. 2004/244075.

In one embodiment, after incubation on medium containing antibiotics to inhibit *Agrobacterium* or *Rhizobium* growth without selective agents (delay medium), the explants are cultured on selective growth medium including, but not limited to, a callus-inducing medium containing a plant cell selective agent. Typical selective agents have been described and include, but are not limited to, antibiotics such as G418, paromomycin, kanamycin, or other chemicals such as glyphosate, dicamba, and glufosinate. The plant tissue cultures surviving the selection medium are subsequently transferred to a regeneration medium suitable for the production of transformed plantlets. Regeneration can be carried out over several steps. Those of skill in the art are aware of the numerous types of media and transfer requirements that can be implemented and optimized for each plant system for plant transformation and regeneration.

The transformants produced are subsequently analyzed to determine the presence or absence of a particular nucleic acid of interest contained on the transformation vector. Molecular analyses can include, but are not limited to, Southern blots or PCR (polymerase chain reaction) analyses. These and other well known methods can be performed to confirm the stability of the transformed plants produced by the methods disclosed, as well as the copy number of insertions, and the presence of vector backbone sequences flanking the T-DNA. These methods are well known to those of skill in the art and have been reported (see, for example, Sambrook et al., 1989).

The previous discussion is merely a broad outline of standard transformation and regeneration protocols. One of skill in the art knows that specific crops and specific protocols can vary somewhat from the broad outline. A variety of media can be used in each system as well. Those of skill in the art are familiar with the variety of tissue culture media that, when supplemented appropriately, support plant tissue growth and development. These tissue culture media can either be purchased as a commercial preparation or custom prepared and modified by those of skill in the art. Examples of such media include, but are not limited to those described by Murashige and Skoog (1962); Chu et al. (1975); Linsmaier and Skoog (1965); Uchimiya and Murashige (1962); Gamborg et al. (1968); Duncan et al. (1985); McCown and Lloyd (1981); Nitsch and Nitsch (1969); and Schenk and Hildebrandt (1972), or derivations of these media supplemented accordingly. Those of skill in the art are aware that media and media supplements such as nutrients and growth regulators for use in transformation and regeneration are usually optimized for the particular target crop or variety of interest. Reagents are commercially available and can be purchased from a number of suppliers (see, for example Sigma Chemical Co., St. Louis, Mo.).

"Overdrive" sequences have been identified in numerous Ti plasmids, including pTiA6, pTiAB3, and pTi15955. Other sequences with high similarity to overdrive or TSS can be identified, for example, using the "BestFit," "Gap," or "FASTA" programs of the Sequence Analysis Software Package, Genetics Computer Group, Inc., University of Wisconsin Biotechnology Center, Madison, Wis. 53711, or using the "BLAST" program (Altschul et al., 1990), or another available DNA sequence analysis package. Such sequences when present in multicopy near an RB sequence may be assayed for transformation enhancement activity, similarly to the sequences whose enhancer activity is described below.

"Frequency of transformation" or "transformation frequency," as used herein, refers to the percentage of transgenic events produced per explant or the percentage of transgenic plants produced per explant.

"Border sequence," e.g. right border (RB) or left border (LB), refers to a directly repeated nucleic acid sequence defining an end of the transferred DNA (T-DNA) region, typically about 24 bp in length. Border sequences may be from a Ti or Ri plasmid of *Agrobacterium* sp., or may be plant derived sequences that function similarly.

"T-DNA Border region" refers to the RB or LB sequence and associated flanking sequence, typically about 100 bp in length, and, as found in nature, may include a transformation enhancer sequence.

"Transformation efficiency" as used herein, refers to any improvement, such as increase in transformation frequency and quality events that impact overall efficiency of the transformation process by reducing the amount of resources required to select event for further commercial development.

"Transformation enhancer" as used herein refers to overdrive and TSS sequences.

A first nucleic acid sequence is "operably linked" with a second nucleic acid sequence when the sequences are so arranged that the first nucleic acid sequence affects the function of the second nucleic-acid sequence. Preferably the two sequences are part of a single contiguous nucleic acid molecule. The overdrive or TSS enhancer sequence may be placed immediately adjacent to the border sequence, such as the RB sequence. Alternatively, in certain embodiments the overdrive or TSS sequence is located about 1, 10, 25, 50, 100, 250, 500, 1000 or more nucleotides from the end of the border sequence, including all intermediate ranges. The overdrive sequence may be placed in either orientation relative to the border.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Synthesis of Transformation Enhancer Sequences

1) Synthesis of 4× Overdrive Sequence

To synthesize a 4×30 bp overdrive (OD) sequence (5' caaacaaacatacacagcgacttattcacacaaacaaacatacacagcgacttattc acacaaacaaacatacacagcgacttattcacaca aacaaacatacacagc-gacttattcaca 3'; SEQ ID NO:18), 2×30 bp overdrive primer pair 5' caaacaaacatacacagcgacttattcacacaaacaaacatacacagc-gacttattcaca 3' (Xd463; SEQ ID NO:1) and 5' tgt-gaataagtcgctgtgtatgtttgtttgtgtgaataagtcgctgtgtatgtttgtttg 3' (Xd464; SEQ ID NO:2) were synthesized, mixed and PCR amplified for 20 cycles in the presence of high fidelity PfuTurbo® polymerase from Stratagene (La Jolla, Calif.). The PCR product was fractionated on a 1% Agarose gel, and the portion of the gel corresponding to the size ranging between 100-300 bp was excised, purified and ligated into TOPO Zero blunt PCR vector from Invitrogen (Carlsbad, Calif.). The repeat stacking was confirmed by sequencing. Up to 6× overdrive sequence was observed following PCR, although only 4×30 bp overdrive insert was utilized in subsequent cloning of a multicopy overdrive construct.

2) Synthesis of 18×TSS Sequence

6×8 bp TSS Repeat Primer Pairs:
5' ctgacgaactgacgaactgacgaactgacgaactgacgaactgacgaa 3' (Xd465; SEQ ID NO:3), and 5' ttcgtcagttcgtcagttcgtcagt-tcgtcagttcgtcagttcgtcag 3' (Xd466; SEQ ID NO:4) were synthesized and equally mixed and amplified for 5 cycles in the presence of Pfu Turbo® polymerase from Stratagene (La Jolla, Calif.). The 100-300 bp size gel slice was cut, purified and ligated into TOPO Zero blunt PCR vector from Invitrogen. Up to 35×TSS repeat was confirmed by sequencing, but only 18×TSS repeat was kept for further cloning. The size of overdrive and TSS was dependent on the PCR cycles and the excised gel position.

Example 2

Construction of Vectors Having RB with Overdrive, Additional Overdrive, or 18×TSS To place the overdrive or TSS in front of a 24 bp RB, an EcoRI site was introduced into a nopaline RB, 11 bp away from the upstream of the RB (of pMON83900). The 4× overdrive or 18×TSS was excised from the corresponding TOPO cloning vector digested by EcoRI and inserted into pMON83900 opened by EcoRI, resulting in pMON83903 and pMON83909, respectively.

The modified RB containing either 4× overdrive or the 18×TSS from pMON83903 or pMON83909 were digested with HindIII/SpeI and used to replace the 1× overdrive RB of pMON83902 with the HindIII/SpeI fragment comprising the 4× overdrive or 18×TSS enhancer sequences, resulting in pMON87462 and pMON83864, respectively, for soy transformation. Alternatively, the RB of pMON80105 was modified so as to comprise the 4× overdrive or 18× TSS by inserting the SpeI/SalI fragment from pMON83903 or pMON83909 to yield pMON87465 and pMON87466, respectively, for corn transformation. The modified RB with 1×, 4× and 18× transformation enhancer sequences are shown in FIGS. 1 and 4 and SEQ ID NOs:14-16.

A construct containing 1× overdrive sequence (SEQ ID NO:17) was synthesized by first assembling the oligonucleotide containing the 30 bp overdrive sequence according to standard protocol and then cloning it into pBlueScript®II (Stratagene Inc., La Jolla, Calif.), resulting in pMON80088. Then the SpeI and NotI (filled-in with polymerase) fragment from pMON80088 was inserted into pMON80105 digested with SpeI and SmaI, resulting into pMON80121 for corn transformation. For soybean transformation, 1× overdrive RB construct, pMON83902, was made by replacing the RB in pMON83898 with the 1× overdrive RB fragment from pMON80121 using PmeI/NdeI restriction enzyme sites.

Example 3

Transformation of Corn with Overdrive or TSS-Enhanced RB Sequences

Corn (*Zea mays*) cells were transformed with oriV containing vectors pMON80105, pMON80121, pMON87465, or pMON87466 essentially as described in U.S. Patent Application Publn. 2004/244075 in order to assess the ability of stacking of additional overdrive and TSS enhancer sequences to improve transformation frequency and the proportion of events comprising low copy number T-DNA insertion and lacking vector backbone sequence (e.g. *E. coli*-derived oriV). The control treatment consisted of transformation with pMON80105, lacking an overdrive or TSS sequence. As shown in Table 1, use of constructs comprising stacked enhancer sequences resulted in a statistically significant increase in transformation frequency. With these constructs, a higher percentage of quality TF was also obtained. Quality TF combines TF and events with one or two copies. Also, the percentage of events having one or two copies increased.

TABLE 2

Effect of transformation enhancer sequences on transformation frequency in soybean.

| Enhancer sequence | pMON plasmid | Transformation frequency (%) |
|---|---|---|
| Control | 83898 | 2.79 |
| 1X overdrive | 83902 | 3.06 |
| 4X overdrive | 87462 | 4.22* |
| 18X TSS | 87464 | 4.10* |

*statistically significant increase

TABLE 3

Effect of transformation enhancer sequences on event quality.

| pMON plasmid | Total events | oriV positive/ total GOI positive | oriV negative/ total GOI positive | 1 copy/oriV negative | 1 or 2 copy regardless of oriV presence or absence |
|---|---|---|---|---|---|
| 83898 (control) | 31 | 6/24 (25%) | 18/24 (75%) | 1 (4%) | 19 (79%) |
| 83902 (1X OD) | 61 | 16/45 (35.5%) | 29/45 (64.5%) | 6 (13.3%) | 30 (66.7%) |
| 87462 (4X OD) | 43 | 12/33 (36.4%) | 21/33 (63.6%) | 4 (12.1%) | 23 (69.7%) |
| 87464 (18X TSS) | 71 | 10/50 (20%) | 40/50 (80%) | 17 (34%) | 37 (74%) |

TABLE 1

Effect of transformation enhancer sequences on transformation frequency and event quality in corn.

| Overdrive in RB | Construct (pMON) | % Transformation Frequency (TF)$^a$ | % Quality TF | % of one or two copies events regardless of backbone |
|---|---|---|---|---|
| 4X OD | 87465 | 25.3 | 12.7% | 50.1 |
| 1X OD | 80121 | 24.1 | 10.4% | 43.2 |
| 18X TSS | 87466 | 22.8 | 10.2% | 44.7 |
| Control | 80105 | 17.7 | 6.4% | 39.0 |

$^a$denotes statistical significance

Example 4

Transformation of Soybean with Overdrive or TSS-Enhanced RB Sequences

Soybean (*Glycine max*) cells were transformed with oriV containing vectors pMON83898, pMON83902, pMON87462, or pMON87464 essentially as described in U.S. Pat. No. 6,384,301 in order to assess the ability of stacking of additional overdrive and TSS enhancer sequences to improve transformation frequency and the proportion of events comprising low copy number T-DNA insertion and lacking vector backbone sequence (e.g. *E. coli*-derived oriV). The sequences of the stacked 4x overdrive and 18xTSS enhancers are found in SEQ ID NO:10 and SEQ ID NO:11, respectively. The control treatment consisted of transformation with pMON83898, lacking an overdrive or TSS sequence. As shown in Tables 2-3, use of constructs comprising stacked transformation enhancer sequences resulted in an increase in transformation frequency. The proportion of single copy and backbone free events also increased (Table 3; column 5). Also, the percentage of events having one or two copies increased.

Example 5

Additional Transformation Enhancer Sequences

In addition to the overdrive sequence of pTiA6 used above (SEQ ID NO:17), other overdrive sequences (including the reverse complementary sequences) are known in the art (e.g. Shurvinton and Ream, 1991), and may be used similarly. These sequences may include but are not limited to those from pTiAB3 (GenBank M63056) (TGTGAATAAATCGCTGTGTATGTTTGTTTG; SEQ ID NO:8), and pTi15955 (GenBank AF242881) (TTGTCTAAATTTCTGTATTTGTTTGTTTG; SEQ ID NO:9), and the consensus sequence AAACAAACATACACAGCGACTTATTCACA (SEQ ID NO:13), and TAARTYNCTGTRTNTGTTTGTTTG; (SEQ ID NO:19, Toro et al., 1988) among others. Primers may be synthesized accordingly and PCR carried out as described in Example 1 to create DNA segments comprising these sequences for use in construction of recombinant plasmids analogous to pMON83902, pMON80121, pMON87462, and pMON87465, among others. Crop plants can be transformed with constructs comprising one or more of these transformation enhancer sequences and can be assessed for their ability to improve transformation frequency and the proportion of events comprising low copy number T-DNA insertion and lacking vector backbone sequence.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 5,004,863; U.S. Pat. No. 5,094,945; U.S. Pat. No. 5,107,065; U.S. Pat. No. 5,159,135; U.S. Pat. No. 5,273,894; U.S. Pat. No. 5,276,268; U.S. Pat. No. 5,561,236; U.S. Pat. No. 5,569,834; U.S. Pat. No. 5,591,616; U.S. Pat. No. 5,627,061; U.S. Pat. No. 5,633,435; U.S. Pat. No. 5,637,489; U.S. Pat. No. 5,646,024; U.S. Pat. No. 5,750,871; U.S. Pat. No. 5,846,797, U.S. Pat. No. 5,981,840; U.S. Pat. No. 6,040,497; U.S. Pat. No. 6,506,559; U.S. Pat. No. 6,624,344; U.S. Pat. No. 6,384,301; U.S. Pat. No. 7,022,896; U.S. Pat. No. 7,060,876.

U.S. patent Ser. No. 09/084,942; U.S. patent Ser. No. 09/127,735; U.S. patent Ser. No. 09/423,143

U.S. Patent Pub. 2002/0168707 A1; U.S. Patent Pub. 2003/0188345; U.S. Patent Pub. 2004/0140376; U.S. Patent Pub. 2004/244075; U.S. Patent Pub. 2006/0041956

Altschul et al., *J. Mol. Biol.*, 215:403-410, 1990.
Barker et al., *Plant Mol. Biol.*, 2:335-350, 1983.
Bird et al., *Biotech Gen. Engin. Rev.*, 9: 207-227, 1991.
Canaday et al., *Mol. Gen. Genet.*, 235:292-303, 1992.
Chu et al., *Scientia Sinica* 18:659, 1975.
Close et al., *J. Bacteriol.*, 169(11):5113-5118, 1987.
Culianez-Macia and Hepburn, *Pl. Mol. Biol.*, 11:389-399, 1988.
Dekeyser et al., *Pl. Physiol.*, 90:217-223, 1989.
Della-Cioppa et al., *Bio/Technology*, 5 579-584, 1987.
Depicker et al., *J. Mol. Appl. Genet.* 1:561-573, 1982.
Duncan et al., *Planta*, 165:322-332, 1985.
Gamborg et al., *Exp. Cell Res.*, 50:151, 1968.
Gelvin, *Microbiol. Molec. Biol. Rev.*, 67:16-37, 2003.
Gibson and Shillitoe, *Mol. Biotech.*, 7:125-137, 1997.
Hansen et al., *Plant Mol. Biol.*, 20(1):113-122, 1992.
Jen and Chilton, *Proc. Natl. Acad. Sci. USA*, 83(11):3895-3899, 1986.
Joersbo et al., *Mol. Breed.*, 4:111-117, 1998.
Kononov et al., *Plant J.* 11:945-957, 1997.
Linsmaier and Skoog, *Physiol. Plant.*, 18 100, 1965.
McCown and Lloyd, *HortScience*, 16:453, 1981.
Mild and McHugh, *J. Biotechnol.*, 107:193, 2004.
Murashige and Skoog, *Physiol. Plant*, 15: 473-497, 1962.
Nitsch and Nitsch, *Science*, 163:85-87, 1969.
PCT Appln. WO 01/44482; PCT Appln. WO 02/00900; PCT Appln. WO 04/074443; PCT Appln. WO 04/009761; PCT Appln. WO 05/121346; PCT Appln. WO 05/107437; PCT Appln. WO 95/06722; PCT Appln. WO 97/48814; PCT Appln. WO 98/53083; PCT Appln. WO 99/53050; PCT Appln. WO 99/61631
Peralta et al., *EMBO J.* 5(6):1137-1142, 1986.).
Rommens et al., *Plant Physiol.*, 139:1338-49, 2005.
Rommens, *Trends Plant Sci.*, 9:457-64, 2004a.
Rommens et al., *Plant Physiol.*, 135:421-31, 2004b.
Sambrook et al., Molecular Cloning: A Laboratory Manual, Second Edition, Cold Spring Harbor Laboratory Press, Cold Spring Harbor, N.Y., 1989.
Schenk and Hildebrandt, *Can. J. Bot.*, 50: 199-204, 1972.
Shaw et al., *Nucleic Acids Res.*, 12(15):6031-6041, 1984.
Shurvinton and Ream, *J Bacteriol.*, 173(17):5558-5563, 1991.
Slighton et al., *EMBO J.*, 4(12):3069-3077, 1985.
Toro et al., *J. Bacteriol.*, 171(12):6845-6859, 1989.
Toro et al., *Proc. Natl. Acad. Sci. USA*, 85:8558-8562, 1988.
Uchimiya and Murashige, *Plant Physiol.* 15:73, 1962.
Van Haaren et al., *Nucleic Acids Res.*, 15(21):8983-8997, 1987a.
Van Haaren et al., *Plant Mol. Biol.*, 11:773-781, 1988.
Van Haaren et al., *Plant Mol. Biol.*, 8:95-104, 1987b.
Wang et al., *Cell*, 38:455-462 1984.
Zhang et al., *Plant Cell, Tissue, and Organ Culture* 56:37-46, 1999.

What is claimed is:

1. A method of producing a recombinant construct comprising:
introducing at least one additional transformation enhancer sequence into a plant transformation vector, said plant transformation vector comprising at least one T-DNA border region, and said T-DNA border region including a transformation enhancer sequence, thereby producing a recombinant construct comprising at least two transformation enhancer sequences, wherein the transformation enhancer sequences are operably linked to the T-DNA border region and comprise two or more copies of SEQ ID NO:20.

2. A recombinant DNA construct comprising a T-DNA border sequence, operably linked to a transformation enhancer sequence, wherein the transformation enhancer sequence comprises two or more copies of SEQ ID NO:20.

3. The construct of claim 2, wherein the border sequence is a right border (RB) sequence.

4. The construct of claim 2, wherein the border sequence is a left border (LB) sequence.

5. The construct of claim 3, wherein the RB sequence is from a nopaline Ti plasmid.

6. The construct of claim 3, wherein the RB sequence is from an octopine Ti plasmid.

7. A transgenic cell transformed with the construct of claim 2.

8. The cell of claim 7, defined as a plant or bacterial cell.

9. The cell of claim 8, wherein the cell is an *Agrobacterium* cell.

10. The cell of claim 8, wherein the cell is a *Rhizobium* cell.

11. The cell of claim 8, wherein the cell is a plant cell from a plant selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato, and watermelon.

12. A transgenic plant transformed with the construct of claim 2.

13. The transgenic plant of claim 12, wherein the transgenic plant is selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato, and watermelon.

14. The method of claim 1, wherein the border region is a right border (RB) sequence.

15. The method of claim 1, wherein the border region is a left border (LB) sequence.

16. The method of claim 1, further comprising transforming a plant cell with said recombinant construct by *Rhizobia*-mediated transformation, wherein the *Rhizobia* bacterium is competent for the transformation of said plant cell.

17. The method of claim 16, wherein the *Rhizobia*-mediated transformation is *Agrobacterium*-mediated transformation.

18. The method of claim 16, wherein the *Rhizobia*-mediated transformation is *Agrobacterium*-, *Rhizobium*-, *Sinorhizobium*-, *Mesorhizobium*-, or *Bradyrhizobium*-mediated transformation.

19. The method of claim 16, wherein the plant cell is from a plant selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato and watermelon.

20. The method of claim 19, wherein the plant cell is a corn or soybean cell.

21. The method of claim 1, wherein the recombinant construct comprises from 2 to about 18 copies of SEQ ID NO:20.

22. The method of claim 16, further comprising regenerating a transgenic plant from said plant cell.

23. The method of claim 1, wherein the transformation enhancer sequences comprise one or more copies of a sequence selected from the group consisting of: SEQ ID NO:7, SEQ ID NO:8, SEQ ID NO:9, and SEQ ID NO:13.

24. A method of producing a recombinant construct comprising:
introducing at least one additional transformation enhancer sequence into a plant transformation vector, said plant transformation vector comprising at least one T-DNA border region, and said T-DNA border region including a first transformation enhancer sequence, thereby producing a recombinant construct comprising at least two transformation enhancer sequences, wherein the transformation enhancer sequences are operably linked to the T-DNA border region and comprise one or more copies of SEQ ID NO:6 and one or more copies of SEQ ID NO:20.

25. The method of claim 24, wherein the border region is a right border (RB) sequence.

26. The method of claim 24, wherein the border region is a left border (LB) sequence.

27. The method of claim 24, further comprising transforming a plant cell with said recombinant construct by *Rhizobia*-mediated transformation, wherein the *Rhizobia* bacterium is competent for the transformation of said plant cell.

28. The method of claim 27, wherein the *Rhizobia*-mediated transformation is *Agrobacterium*-mediated transformation.

29. The method of claim 27, wherein the *Rhizobia*-mediated transformation is *Agrobacterium*-, *Rhizobium*-, *Sinorhizobium*-, *Mesorhizobium*-, or *Bradyrhizobium*-mediated transformation.

30. The method of claim 27, wherein the plant cell is from a plant selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato and watermelon.

31. The method of claim 30, wherein the plant cell is a corn or soybean cell.

32. The method of claim 27, further comprising regenerating a transgenic plant from said plant cell.

33. A recombinant DNA construct comprising a T-DNA border sequence operably linked to a transformation enhancer sequence, wherein the transformation enhancer sequence comprises a combination of one or more copies of SEQ ID NO:6 and one or more copies of SEQ ID NO:20.

34. The construct of claim 33, wherein the border sequence is a right border (RB) sequence.

35. The construct of claim 33, wherein the border sequence is a left border (LB) sequence.

36. The construct of claim 34, wherein the RB sequence is from a nopaline Ti plasmid.

37. The construct of claim 34, wherein the RB sequence is from an octopine Ti plasmid.

38. The construct of claim 33, wherein the transformation enhancer sequence comprises one or more copies of a sequence selected from the group consisting of: SEQ ID NO:7, SEQ ID NO:8, SEQ ID NO:9, and SEQ ID NO:13.

39. A transgenic cell transformed with the construct of claim 33.

40. The cell of claim 39, defined as a plant or bacterial cell.

41. The cell of claim 40, wherein the cell is an *Agrobacterium* cell.

42. The cell of claim 40, wherein the cell is a *Rhizobium* cell.

43. The cell of claim 40, wherein the cell is a plant cell from a plant selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato, and watermelon.

44. A transgenic plant transformed with the construct of claim 33.

45. The transgenic plant of claim 44, wherein the transgenic plant is selected from the group consisting of soybean, corn, cotton, canola, rice, wheat, alfalfa, common bean, peanut, tobacco, sunflower, barley, beet, broccoli, cabbage, carrot, cauliflower, celery, Chinese cabbage, cucumber, eggplant, leek, lettuce, melon, oat, onion, pea, pepper, peanut, potato, pumpkin, radish, sorghum, spinach, squash, sugarbeet, tomato, and watermelon.

* * * * *

SEQUENCE LISTING

```
<160> NUMBER OF SEQ ID NOS: 20

<210> SEQ ID NO 1
<211> LENGTH: 60
<212> TYPE: DNA
<213> ORGANISM: Artificial sequence
<220> FEATURE:
<223> OTHER INFORMATION: Synthetic primer

<400> SEQUENCE: 1
caaacaaaca tacacagcga cttattcaca caaacaaaca tacacagcga cttattcaca      60

<210> SEQ ID NO 2
<211> LENGTH: 60
<212> TYPE: DNA
<213> ORGANISM: Artificial sequence
<220> FEATURE:
<223> OTHER INFORMATION: Synthetic primer

<400> SEQUENCE: 2
tgtgaataag tcgctgtgta tgtttgtttg tgtgaataag tcgctgtgta tgtttgtttg      60

<210> SEQ ID NO 3
```

```
<211> LENGTH: 48
<212> TYPE: DNA
<213> ORGANISM: Artificial sequence
<220> FEATURE:
<223> OTHER INFORMATION: Synthetic primer

<400> SEQUENCE: 3
ctgacgaact gacgaactga cgaactgacg aactgacgaa ctgacgaa                         48

<210> SEQ ID NO 4
<211> LENGTH: 48
<212> TYPE: DNA
<213> ORGANISM: Artificial sequence
<220> FEATURE:
<223> OTHER INFORMATION: Synthetic primer

<400> SEQUENCE: 4
ttcgtcagtt cgtcagttcg tcagttcgtc agttcgtcag ttcgtcag                         48

<210> SEQ ID NO 5
<211> LENGTH: 24
<212> TYPE: DNA
<213> ORGANISM: Agrobacterium tumefaciens

<400> SEQUENCE: 5
taagtcgctg tgtatgtttg tttg                                                   24

<210> SEQ ID NO 6
<211> LENGTH: 8
<212> TYPE: DNA
<213> ORGANISM: Agrobacterium rhizogenes

<400> SEQUENCE: 6 ctgacgaa                                                                      8

<210> SEQ ID NO 7
<211> LENGTH: 30
<212> TYPE: DNA
<213> ORGANISM: Agrobacterium tumefaciens

<400> SEQUENCE: 7
tgtgaataag tcgctgtgta tgtttgtttg                                             30

<210> SEQ ID NO 8
<211> LENGTH: 30
<212> TYPE: DNA
<213> ORGANISM: Agrobacterium tumefaciens

<400> SEQUENCE: 8
tgtgaataaa tcgctgtgta tgtttgtttg                                             30

<210> SEQ ID NO 9
<211> LENGTH: 30
<212> TYPE: DNA
<213> ORGANISM: Agrobacterium tumefaciens

<400> SEQUENCE: 9
tgtgaataag tcgctgtgta tgtttgtttg                                             30

<210> SEQ ID NO 10
<211> LENGTH: 120
<212> TYPE: DNA
<213> ORGANISM: Artificial sequence
<220> FEATURE:
<223> OTHER INFORMATION: Synthetic primer
```

```
<400> SEQUENCE: 10
tgtgaataag tcgctgtgta tgtttgtttg tgtgaataag tcgctgtgta tgtttgtttg      60
tgtgaataag tcgctgtgta tgtttgtttg tgtgaataag tcgctgtgta tgtttgtttg     120

<210> SEQ ID NO 11
<211> LENGTH: 144
<212> TYPE: DNA
<213> ORGANISM: Agrobacterium rhizogenes

<400> SEQUENCE: 11
ctgacgaact gacgaactga cgaactgacg aactgacgaa ctgacgaact gacgaactga      60
cgaactgacg aactgacgaa ctgacgaact gacgaactga cgaactgacg aactgacgaa     120
ctgacgaact gacgaactga cgaa                                            144

<210> SEQ ID NO 12
<211> LENGTH: 80
<212> TYPE: DNA
<213> ORGANISM: Agrobacterium tumefaciens

<400> SEQUENCE: 12
tgatgatgct gactggcagg atatataccg ttgtaatttg agctcgtgtg aataagtcgc      60
tgtgtatgtt tgtttgattg                                                  80

<210> SEQ ID NO 13
<211> LENGTH: 29
<212> TYPE: DNA
<213> ORGANISM: Artificial sequence
<220> FEATURE:
<223> OTHER INFORMATION: Synthetic primer

<400> SEQUENCE: 13
aaacaaacat acacagcgac ttattcaca                                        29

<210> SEQ ID NO 14
<211> LENGTH: 387
<212> TYPE: DNA
<213> ORGANISM: Artificial sequence
<220> FEATURE:
<223> OTHER INFORMATION: Synthetic primer

<400> SEQUENCE: 14
aggatttttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc cgattattct aataaacgct ctttcaaaca aacatacaca     300
gcgacttatt cacatctctt aggtttaccc gccaatatat cctgtcaaac actgatagtt     360
taaactgaag gcgggaaacg acaatct                                         387

<210> SEQ ID NO 15
<211> LENGTH: 499
<212> TYPE: DNA
<213> ORGANISM: Artificial sequence
<220> FEATURE:
<223> OTHER INFORMATION: Synthetic primer

<400> SEQUENCE: 15
```

```
aggattttc  ggcgctgcgc  tacgtccgcg  accgcgttga  gggatcaagc  cacagcagcc   60
cactcgacct  tctagccgac  ccagacgagc  caagggatct  ttttggaatg  ctgctccgtc  120
gtcaggcttt  ccgacgtttg  ggtggttgaa  cagaagtcat  tatcgcacgg  aatgccaagc  180
actcccgagg  ggaaccctgt  ggttggcatg  cacatacaaa  tggacgaacg  gataaacctt  240
ttcacgccct  tttaaatatc  cgattattct  aataaacgct  ctttgaattc  gcccttcaaa  300
caaacataca  cagcgactta  ttcacacaaa  caaacataca  cagcgactta  ttcacacaaa  360
caaacataca  cagcgactta  ttcacacaaa  caaacataca  cagcgactta  ttcacaaagg  420
gcgaattctc  ttaggtttac  ccgccaatat  atcctgtcaa  acactgatag  tttaaactga  480
aggcgggaaa  cgacaatct                                                   499
```

<210> SEQ ID NO 16
<211> LENGTH: 521
<212> TYPE: DNA
<213> ORGANISM: Artificial sequence
<220> FEATURE:
<223> OTHER INFORMATION: Synthetic primer

<400> SEQUENCE: 16

```
aggattttc  ggcgctgcgc  tacgtccgcg  accgcgttga  gggatcaagc  cacagcagcc   60
cactcgacct  tctagccgac  ccagacgagc  caagggatct  ttttggaatg  ctgctccgtc  120
gtcaggcttt  ccgacgtttg  ggtggttgaa  cagaagtcat  tatcgcacgg  aatgccaagc  180
actcccgagg  ggaaccctgt  ggttggcatg  cacatacaaa  tggacgaacg  gataaacctt  240
ttcacgccct  tttaaatatc  cgattattct  aataaacgct  ctttgaattc  gcccttctga  300
cgaactgacg  aactgacgaa  ctgacgaact  gacgaactga  cgaactgacg  aactgacgaa  360
ctgacgaact  gacgaactga  cgaactgacg  aactgacgaa  ctgacgaact  gacgaactga  420
cgaactgacg  aactgacgaa  gggcgaattc  tcttaggttt  acccgccaat  atatcctgtc  480
aaacactgat  agtttaaact  gaaggcggga  aacgacaatc  t                      521
```

<210> SEQ ID NO 17
<211> LENGTH: 30
<212> TYPE: DNA
<213> ORGANISM: Artificial sequence
<220> FEATURE:
<223> OTHER INFORMATION: Synthetic primer

<400> SEQUENCE: 17

```
caaacaaaca  tacacagcga  cttattcaca                                       30
```

<210> SEQ ID NO 18
<211> LENGTH: 120
<212> TYPE: DNA
<213> ORGANISM: Artificial sequence
<220> FEATURE:
<223> OTHER INFORMATION: Synthetic primer

<400> SEQUENCE: 18

```
caaacaaaca  tacacagcga  cttattcaca  caaacaaaca  tacacagcga  cttattcaca   60
caaacaaaca  tacacagcga  cttattcaca  caaacaaaca  tacacagcga  cttattcaca  120
```

<210> SEQ ID NO 19
<211> LENGTH: 24
<212> TYPE: DNA
<213> ORGANISM: Artificial sequence
<220> FEATURE:
<223> OTHER INFORMATION: Synthetic primer

```
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 19
taartynctg trtntgtttg tttg                                          24

<210> SEQ ID NO 20
<211> LENGTH: 8
<212> TYPE: DNA
<213> ORGANISM: Artificial sequence
<220> FEATURE:
<223> OTHER INFORMATION: Synthetic primer

<400> SEQUENCE: 20 tgtwtgtk                                                             8
```